US012416600B2

(12) United States Patent
Ogiso et al.

(10) Patent No.: US 12,416,600 B2
(45) Date of Patent: Sep. 16, 2025

(54) SENSOR ELEMENT OF GAS SENSOR AND METHOD FOR FORMING PROTECTIVE LAYER OF SENSOR ELEMENT

(71) Applicant: NGK INSULATORS, LTD., Nagoya (JP)

(72) Inventors: Yusuke Ogiso, Nagoya (JP); Yoshimasa Kondo, Nagoya (JP); Katsunao Uenishi, Nagakute (JP)

(73) Assignee: NGK INSULATORS, LTD., Nagoya (JP)

( * ) Notice: Subject to any disclaimer, the term of this patent is extended or adjusted under 35 U.S.C. 154(b) by 547 days.

(21) Appl. No.: 17/736,219

(22) Filed: May 4, 2022

(65) Prior Publication Data

US 2022/0260518 A1 Aug. 18, 2022

Related U.S. Application Data

(63) Continuation of application No. PCT/JP2020/045674, filed on Dec. 8, 2020.

(30) Foreign Application Priority Data

Dec. 17, 2019 (JP) .................................. 2019-227572

(51) Int. Cl.
  *G01N 27/407* (2006.01)
  *G01N 33/00* (2006.01)
(52) U.S. Cl.
  CPC ..... *G01N 27/4071* (2013.01); *G01N 27/4075* (2013.01); *G01N 33/0037* (2013.01)
(58) Field of Classification Search
  CPC ........... G01N 27/4071; G01N 27/4075; G01N 27/4077; G01N 33/0037
  See application file for complete search history.

(56) References Cited

U.S. PATENT DOCUMENTS 10,315,961 B2   6/2019 Tomita et al.
2012/0211362 A1* 8/2012 Onkawa ............. G01N 27/4077
                                                     204/424

(Continued)

FOREIGN PATENT DOCUMENTS

JP    2012-173146 A   9/2012
JP    2012-173147 A   9/2012

(Continued)

OTHER PUBLICATIONS

International Search Report of PCT/JP2020/045674 dated Jan. 19, 2021.

*Primary Examiner* — Luan V Van
*Assistant Examiner* — Shizhi Qian
(74) *Attorney, Agent, or Firm* — MATTINGLY & MALUR, PC

(57) ABSTRACT

A sensor element includes: an element base which has a gas inlet in one end portion thereof and into which a measurement gas is introduced through the gas inlet; and a leading-end protective layer disposed around an outer periphery of the element base in a predetermined range from the one end portion, having a laminated structure of: an inner layer having coarse voids with a size of 1 μm or more in a matrix region having a framework structure formed by porous pieces each having fine pores with a pore diameter of 10 nm or more and less than 1 μm; and an outer layer disposed to cover the inner leading-end protective layer, and having a lower porosity than the inner layer, and the inner layer has: an overall porosity of 40% or more and 90% or less; and a coarse porosity of 1% or more and 55% or less.

19 Claims, 11 Drawing Sheets

(56) References Cited

U.S. PATENT DOCUMENTS

| | | | |
|---|---|---|---|
| 2013/0104625 A1* | 5/2013 | Otsuka | G01N 33/0037 |
| | | | 73/23.31 |
| 2014/0130572 A1 | 5/2014 | Otsuka et al. | |
| 2017/0284958 A1* | 10/2017 | Watanabe | G01N 27/4074 |
| 2020/0309730 A1 | 10/2020 | Hino et al. | |
| 2021/0179496 A1 | 6/2021 | Fujisaki et al. | |
| 2021/0341413 A1 | 11/2021 | Fujisaki et al. | |

FOREIGN PATENT DOCUMENTS

| | | |
|---|---|---|
| JP | 2014-98590 A | 5/2014 |
| JP | 2017-187482 A | 10/2017 |
| JP | 6407887 B2 | 10/2018 |
| JP | 2020-165813 A | 10/2020 |
| WO | 2020/065952 A1 | 4/2020 |
| WO | 2020/144827 A1 | 7/2020 |

* cited by examiner

F I G. 1
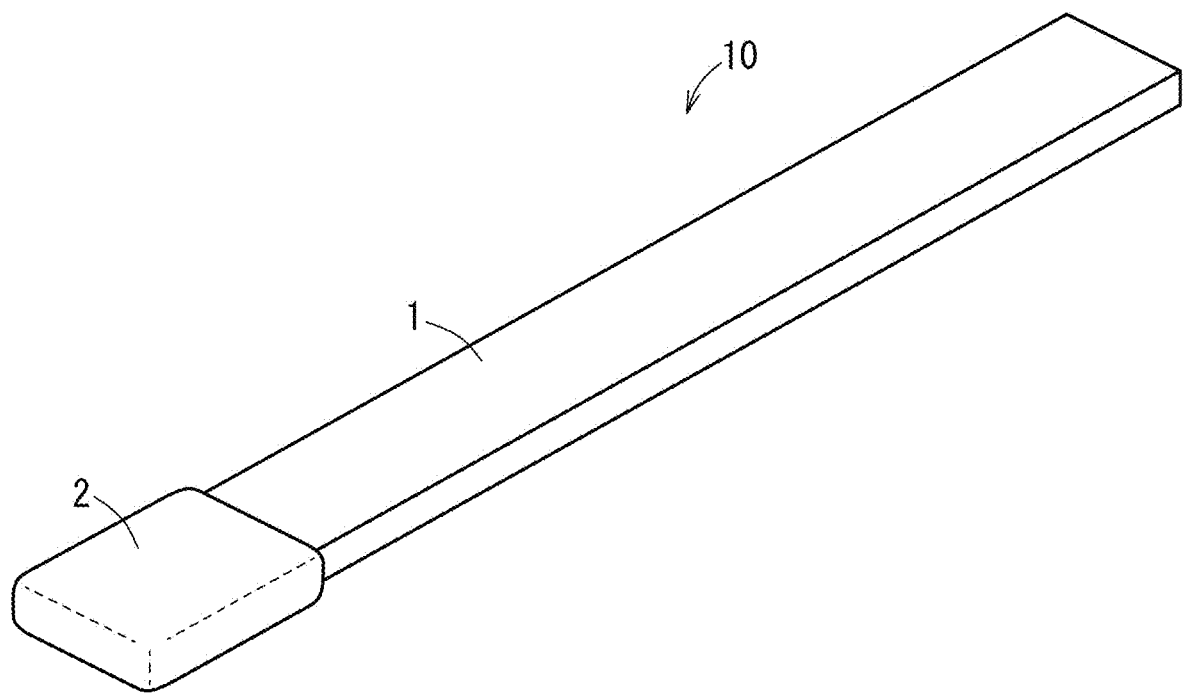

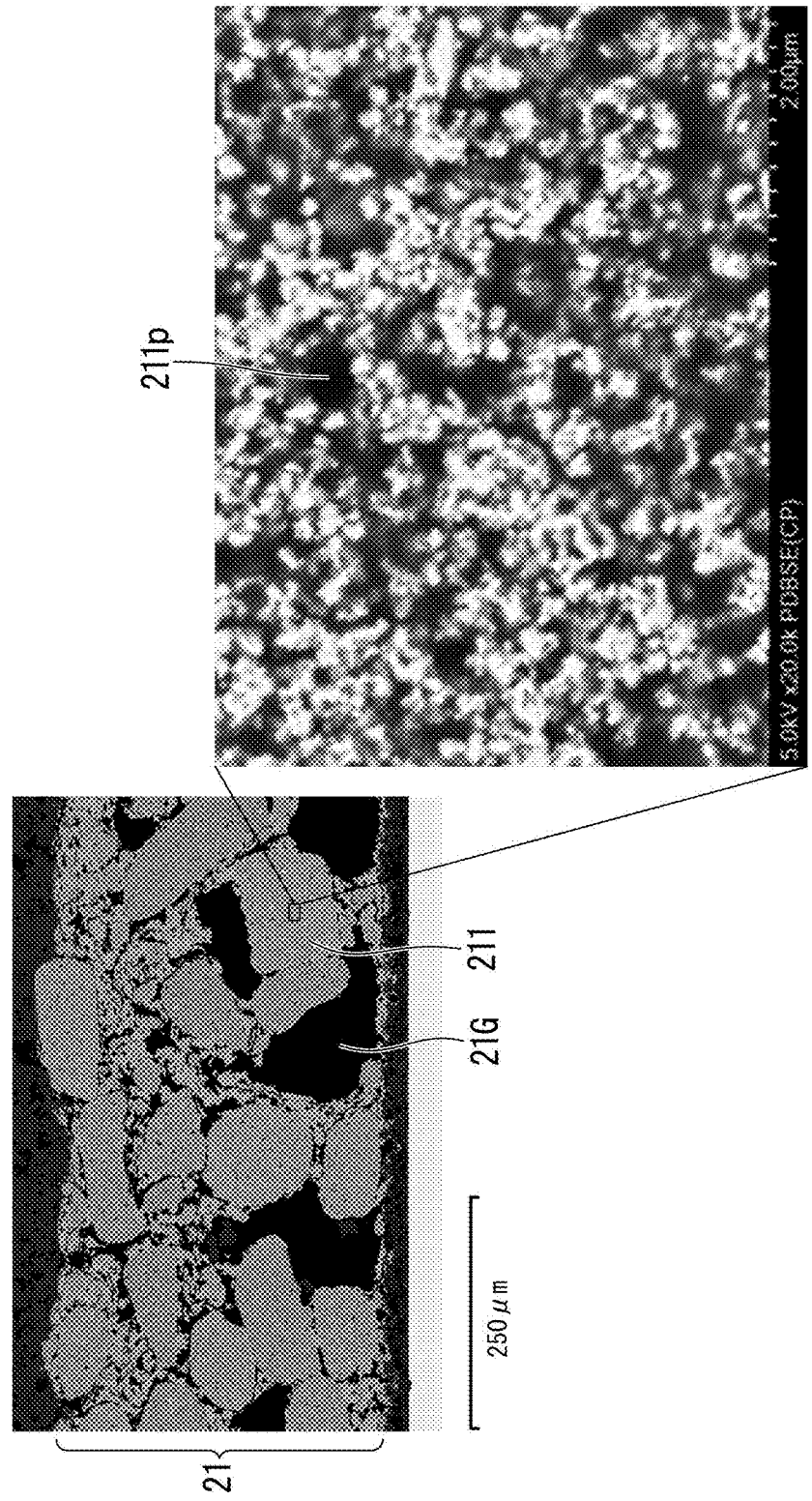
F I G. 4

SENSOR ELEMENT OF GAS SENSOR AND METHOD FOR FORMING PROTECTIVE LAYER OF SENSOR ELEMENT

CROSS-REFERENCE TO RELATED APPLICATION

This application is a continuation application of PCT/JP2020/045674, filed on Dec. 8, 2020, which claims the benefit of priority of Japanese Patent Application No. 2019-227572, filed on Dec. 17, 2019, the entire contents of which are incorporated herein by reference.

BACKGROUND OF THE INVENTION

Field of the Invention

The present invention relates to a sensor element of a gas sensor and, in particular, to a surface protective layer thereof.

Description of the Background Art

As a gas sensor for determining concentration of a desired gas component contained in a measurement gas, such as an exhaust gas from an internal combustion engine, a gas sensor that includes a sensor element (gas sensor element) including some electrodes on the surface and the inside of a base made of an oxygen-ion conductive solid electrolyte, such as zirconia ($ZrO_2$), has been widely known. As the sensor element, a sensor element including a protective layer formed of a porous body (porous protective layer) in an end portion of an elongated planar base in which a part for introducing the measurement gas is provided has been known (see Japanese Patent Application Laid-Open No. 2014-98590, for example).

The protective layer is provided to the surface of the sensor element to secure water resistance of the sensor element when the gas sensor is in use. Specifically, the protective layer is provided to prevent a crack in the surface of the sensor element caused under the action on the sensor element of thermal shock caused by heat (cold) from water droplets adhering to the surface of the sensor element, and further prevent water-induced breakage of the sensor element.

A porous material including, as a framework, zirconia particles and a dissimilar material on the surfaces thereof and having many fine pores with a nano-order pore diameter to have high thermal insulating performance has also already been known (see Japanese Patent No. 6407887, for example).

A protective layer of a conventional sensor element as disclosed in Japanese Patent Application Laid-Open No. 2014-98590 typically has a framework structure formed by many ceramic particles with a submicron to micron-order particle diameter randomly connected (linked) in three dimensions, and voids formed between the ceramic particles function as pores.

The protective layer preferably has high thermal insulating properties (low thermal conductivity) to suppress the water-induced breakage, but, in a case where a protective layer having a configuration as disclosed in Japanese Patent Application Laid-Open No. 2014-98590 is provided, porosity is required to be increased to reduce thermal conductivity. The increase in porosity of the protective layer, however, leads to a lack of strength of the protective layer itself.

An increase in thickness of the protective layer is considered to suppress arrival of thermal shock at an element base and secure the strength of the protective layer, but is not preferable as it increases specific heat (heat capacity) of the sensor element, leading to an increase in element heating-up time.

As a size of voids formed in the protective layer increases, specific heat (heat capacity) of the sensor element decreases to reduce the element heating-up time, but voids with a large size are less likely to be formed in a protective layer as disclosed in Japanese Patent Application Laid-Open No. 2014-98590 due to a material and a manufacturing process thereof.

SUMMARY

The present invention relates to a sensor element of a gas sensor and, in particular, to leading-end protective layer thereof.

According to the present invention, a sensor element of a gas sensor includes: an element base being a ceramic structured body having a gas inlet in one end portion thereof and including therein a gas distribution part communicating from the gas inlet in a longitudinal direction, a measurement gas containing a gas component to be measured being introduced into the gas distribution part through the gas inlet, the gas component to be measured being sensed by a sensing part disposed in the gas distribution part; and a leading-end protective layer disposed around an outer periphery of the element base in a predetermined range from the one end portion, wherein the leading-end protective layer has a laminated structure of: an inner leading-end protective layer having coarse voids with a size of 1 μm or more in a matrix region having a framework structure formed by porous pieces each having fine pores with a pore diameter of 10 nm or more and less than 1 μm; and an outer leading-end protective layer disposed to cover the inner leading-end protective layer, and having a lower porosity than the inner leading-end protective layer, and the inner leading-end protective layer has: an overall porosity of 40% or more and 90% or less; and a coarse porosity of 1% or more and 55% or less, the coarse porosity corresponding to a porosity of the coarse voids.

According to the present invention, the sensor element can have water resistance of 20 μL or more, which is at least the same or higher than that of a conventional sensor element, and heat capacity of the inner leading-end protective layer can be reduced while the strength of the layer itself is secured.

It is therefore an object of the present invention to provide a sensor element of a gas sensor having high water resistance while including a protective layer having reduced thermal conductivity.

BRIEF DESCRIPTION OF DRAWINGS

FIG. 1 is a schematic external perspective view of a sensor element (gas sensor element) 10.

FIG. 4 is a cross-sectional SEM image of a portion of the inner leading-end protective layer 21 and a partial high magnification image thereof.

DESCRIPTION OF EMBODIMENTS

Overview of Sensor Element and Gas Sensor

Figure 2:
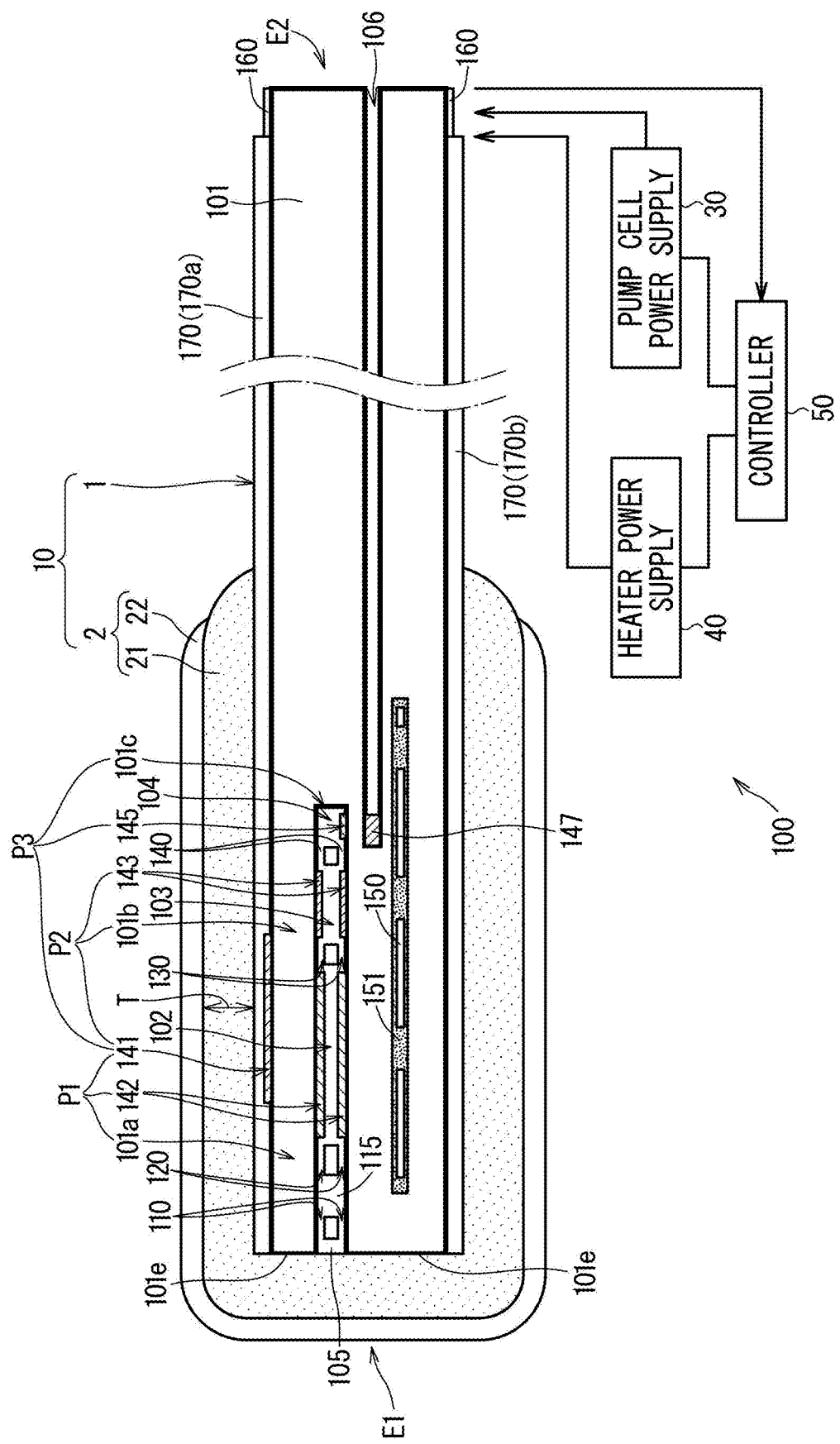
FIG. 2 is a schematic view illustrating a configuration of a gas sensor 100 including a cross-sectional view taken along a longitudinal direction of the sensor element 10.

FIG. 1 is a schematic external perspective view of a sensor element (gas sensor element) 10 according to an embodiment of the present invention. FIG. 2 is a schematic view illustrating a configuration of a gas sensor 100 including a cross-sectional view taken along a longitudinal direction of the sensor element 10. The sensor element 10 is a ceramic structured body as a main component of the gas sensor 100 sensing a predetermined gas component in a measurement gas, and measuring concentration thereof. The sensor element 10 is a so-called limiting current gas sensor element.

In addition to the sensor element 10, the gas sensor 100 mainly includes a pump cell power supply 30, a heater power supply 40, and a controller 50.

As illustrated in FIG. 1, the sensor element 10 has a configuration in which one end portion of an elongated planar element base 1 is covered with a leading-end protective layer 2.

As illustrated in FIG. 2, the element base 1 includes an elongated planar ceramic body 101 as a main structured body, main surface protective layers 170 are provided on two main surfaces of the ceramic body 101, and, in the sensor element 10, the leading-end protective layer 2 is further provided outside both an end surface (a leading end surface 101e of the ceramic body 101) and four side surfaces in one leading end portion. The four side surfaces other than opposite end surfaces in the longitudinal direction of the sensor element 10 (or the element base 1, or the ceramic body 101) are hereinafter simply referred to as side surfaces of the sensor element 10 (or the element base 1, or the ceramic body 101).

The ceramic body 101 is made of ceramics containing, as a main component, zirconia (yttrium stabilized zirconia), which is an oxygen-ion conductive solid electrolyte. Various components of the sensor element 10 are provided outside and inside the ceramic body 101. The ceramic body 101 having the configuration is dense and airtight. The configuration of the sensor element 10 illustrated in FIG. 2 is just an example, and a specific configuration of the sensor element 10 is not limited to this configuration.

The sensor element 10 illustrated in FIG. 2 is a so-called serial three-chamber structure type gas sensor element including a first internal chamber 102, a second internal chamber 103, and a third internal chamber 104 inside the ceramic body 101. That is to say, in the sensor element 10, the first internal chamber 102 communicates, through a first diffusion control part 110 and a second diffusion control part 120, with a gas inlet 105 opening to the outside on a side of one end portion E1 of the ceramic body 101 (to be precise, communicating with the outside through the leading-end protective layer 2), the second internal chamber 103 communicates with the first internal chamber 102 through a third diffusion control part 130, and the third internal chamber 104 communicates with the second internal chamber 103 through a fourth diffusion control part 140. A path from the gas inlet 105 to the third internal chamber 104 is also referred to as a gas distribution part. In the sensor element 10 according to the present embodiment, the distribution part is provided straight along the longitudinal direction of the ceramic body 101.

The first diffusion control part 110, the second diffusion control part 120, the third diffusion control part 130, and the fourth diffusion control part 140 are each provided as two slits vertically arranged in FIG. 2. The first diffusion control part 110, the second diffusion control part 120, the third diffusion control part 130, and the fourth diffusion control part 140 provide predetermined diffusion resistance to a measurement gas passing therethrough. A buffer space 115 having an effect of buffering pulsation of the measurement gas is provided between the first diffusion control part 110 and the second diffusion control part 120.

An outer pump electrode 141 is provided on an outer surface of the ceramic body 101, and an inner pump electrode 142 is provided in the first internal chamber 102. Furthermore, an auxiliary pump electrode 143 is provided in the second internal chamber 103, and a measurement electrode 145 as a sensing part to directly sense a gas component to be measured is provided in the third internal chamber 104. In addition, a reference gas inlet 106 which communicates with the outside and through which a reference gas is introduced is provided on a side of the other end portion E2 of the ceramic body 101, and a reference electrode 147 is provided in the reference gas inlet 106.

In a case where a target of measurement of the sensor element 10 is NOx in the measurement gas, for example, concentration of a NOx gas in the measurement gas is calculated by a process as described below.

First, the measurement gas introduced into the first internal chamber 102 is adjusted to have a substantially constant oxygen concentration by a pumping action (pumping in or out of oxygen) of a main pump cell P1, and then introduced into the second internal chamber 103. The main pump cell P1 is an electrochemical pump cell including the outer pump electrode 141, the inner pump electrode 142, and a ceramic layer 101a that is a portion of the ceramic body 101 existing between these electrodes. In the second internal chamber 103, oxygen in the measurement gas is pumped out of the element by a pumping action of an auxiliary pump cell P2, which is also an electrochemical pump cell, so that the measurement gas is at a sufficiently low oxygen partial pressure. The auxiliary pump cell P2 includes the outer pump electrode 141, the auxiliary pump electrode 143, and a ceramic layer 101b that is a portion of the ceramic body 101 existing between these electrodes.

The outer pump electrode 141, the inner pump electrode 142, and the auxiliary pump electrode 143 are each formed as a porous cermet electrode. The inner pump electrode 142 and the auxiliary pump electrode 143 to be in contact with the measurement gas are each formed using a material having weakened or no reducing ability with respect to a NOx component in the measurement gas.

NOx in the measurement gas caused by the auxiliary pump cell P2 to be at a low oxygen partial pressure is introduced into the third internal chamber 104, and reduced or decomposed by the measurement electrode 145 provided in the third internal chamber 104. The measurement electrode 145 is a porous cermet electrode also functioning as a NOx reduction catalyst that reduces NOx existing in an atmosphere in the third internal chamber 104. During the reduction or decomposition, a potential difference between the measurement electrode 145 and the reference electrode 147 is maintained constant. Oxygen ions generated by the above-mentioned reduction or decomposition are pumped out of the element by a measurement pump cell P3. The measurement pump cell P3 includes the outer pump electrode 141, the measurement electrode 145, and a ceramic layer 101c that is a portion of the ceramic body 101 existing between these electrodes. The measurement pump cell P3 is an electrochemical pump cell pumping out oxygen generated by decomposition of NOx in an atmosphere around the measurement electrode 145.

Pumping (pumping in or out of oxygen) of the main pump cell P1, the auxiliary pump cell P2, and the measurement pump cell P3 is achieved, under control performed by the controller 50, by the pump cell power supply (variable power supply) 30 applying a voltage necessary for pumping across electrodes included in each of the pump cells. In a case of the measurement pump cell P3, a voltage is applied across the outer pump electrode 141 and the measurement electrode 145 so that the potential difference between the measurement electrode 145 and the reference electrode 147 is maintained at a predetermined value. The pump cell power supply 30 is typically provided for each pump cell.

The controller 50 detects a pump current Ip2 flowing between the measurement electrode 145 and the outer pump electrode 141 in accordance with the amount of oxygen pumped out by the measurement pump cell P3, and calculates a NOx concentration in the measurement gas based on a linear relationship between a current value (NOx signal) of the pump current Ip2 and the concentration of decomposed NOx.

The gas sensor 100 preferably includes a plurality of electrochemical sensor cells, which are not illustrated, sensing the potential difference between each pump electrode and the reference electrode 147, and each pump cell is controlled by the controller 50 based on a signal detected by each sensor cell.

In the sensor element 10, a heater 150 is buried in the ceramic body 101. The heater 150 is provided, below the gas distribution part in FIG. 2, over a range from the vicinity of the one end portion E1 at least to a position of formation of the measurement electrode 145 and the reference electrode 147. The heater 150 is provided mainly to heat the sensor element 10 to enhance oxygen-ion conductivity of the solid electrolyte forming the ceramic body 101 when the sensor element 10 is in use. More particularly, the heater 150 is provided to be surrounded by an insulating layer 151.

The heater 150 is a resistance heating body made, for example, of platinum. The heater 150 generates heat by being powered from the heater power supply 40 under control performed by the controller 50.

The sensor element 10 according to the present embodiment is heated by the heater 150 when being in use so that the temperature at least in a range from the first internal chamber 102 to the second internal chamber 103 is at or above 500° C. In some cases, the sensor element 10 is heated so that the temperature of the gas distribution part as a whole from the gas inlet 105 to the third internal chamber 104 is at or above 500° C. These are to enhance the oxygen-ion conductivity of the solid electrolyte forming each pump cell and to desirably demonstrate the ability of each pump cell. In this case, the temperature in the vicinity of the first internal chamber 102, which is at the highest temperature, is approximately at 700° C. to 800° C.

In the following description, from among the two main surfaces of the ceramic body 101, a main surface (or an outer surface of the sensor element 10 having the main surface) which is located on an upper side in FIG. 2 and on a side where the main pump cell P1, the auxiliary pump cell P2, and the measurement pump cell P3 are mainly provided is also referred to as a pump surface, and a main surface (or an outer surface of the sensor element 10 having the main surface) which is located on a lower side in FIG. 2 and on a side where the heater 150 is provided is also referred to as a heater surface. In other words, the pump surface is a main surface closer to the gas inlet 105, the three internal chambers, and the pump cells than to the heater 150, and the heater surface is a main surface closer to the heater 150 than to the gas inlet 105, the three internal chambers, and the pump cells.

A plurality of electrode terminals 160 are formed on the respective main surfaces of the ceramic body 101 on the side of the other end portion E2 to establish electrical connection between the sensor element 10 and the outside. These electrode terminals 160 are electrically connected to the above-mentioned five electrodes, opposite ends of the heater 150, and a lead for detecting heater resistance, which is not illustrated, through leads provided inside the ceramic body 101, which are not illustrated, to have a predetermined correspondence relationship. Application of a voltage from the pump cell power supply 30 to each pump cell of the sensor element 10 and heating by the heater 150 by being powered from the heater power supply 40 are thus performed through the electrode terminals 160.

The sensor element 10 further includes the above-mentioned main surface protective layers 170 (170a and 170b) on the pump surface and the heater surface of the ceramic body 101. The main surface protective layers 170 are layers made of alumina, having a thickness of approximately 5 μm to 30 μm, and having pores with a porosity of approximately 20% to 40%, and are provided to prevent adherence of any foreign matter and poisoning substances to the main surfaces (the pump surface and the heater surface) of the ceramic body 101 and the outer pump electrode 141 provided on the pump surface. The main surface protective layer 170a on the pump surface thus functions as a pump electrode protective layer for protecting the outer pump electrode 141.

The main surface protective layers 170 are provided over substantially all of the pump surface and the heater surface except that the electrode terminals 160 are partially exposed in FIG. 2, but this is just an example. The main surface protective layers 170 may locally be provided in the vicinity of the outer pump electrode 141 on the side of the one end portion E1 compared with the case illustrated in FIG. 2.

Leading-End Protective Layer

In the sensor element 10, the leading-end protective layer 2 is provided around an outermost periphery of the element base 1 having a configuration as described above in a predetermined range from the one end portion E1.

The leading-end protective layer 2 is provided in a manner of surrounding a portion of the element base 1 in which the temperature is high (up to approximately 700° C. to 800° C.) when the gas sensor 100 is in use, in order to secure water resistance in the portion to thereby suppress the occurrence of cracking (water-induced breakage) of the element base 1 due to thermal shock caused by local temperature reduction upon direct water wetting.

In addition, the leading-end protective layer 2 is provided to secure poisoning resistance to prevent poisoning substances, such as Mg, from entering into the sensor element 10.

As illustrated in FIG. 2, in the sensor element 10 according to the present embodiment, the leading-end protective layer 2 has a laminated structure of an inner leading-end protective layer (also referred to as an inner protective layer) 21 and an outer leading-end protective layer (also referred to as an outer protective layer) 22.

The inner leading-end protective layer 21 and the outer leading-end protective layer 22 are provided in this order from inside to cover the leading end surface 101e and the four side surfaces on the side of the one end portion E1 of the element base 1 (around an outer periphery of the element base 1 on the side of the one end portion E1). Generally, the inner leading-end protective layer 21 is a layer mainly responsible for suppression of heat transfer from the outside to the element base 1 (securement of thermal insulating properties) leading to securement of water resistance, and the outer leading-end protective layer 22 is a layer mainly responsible for trapping of the poisoning substances and protection of the inner leading-end protective layer 21.

The inner leading-end protective layer 21 is a porous ceramic layer having a framework structure (matrix region) formed by porous pieces each having many fine pores, and having random voids (coarse voids) sufficiently larger than the fine pores of the porous pieces. Details of the inner leading-end protective layer 21 will be described below.

The outer leading-end protective layer 22 is a porous ceramic layer made, for example, of alumina formed by a conventionally known method. The outer leading-end protective layer 22 is provided as a layer having a lower porosity than the inner leading-end protective layer 21.

Details of Inner Leading-End Protective Layer

Figure 3A:
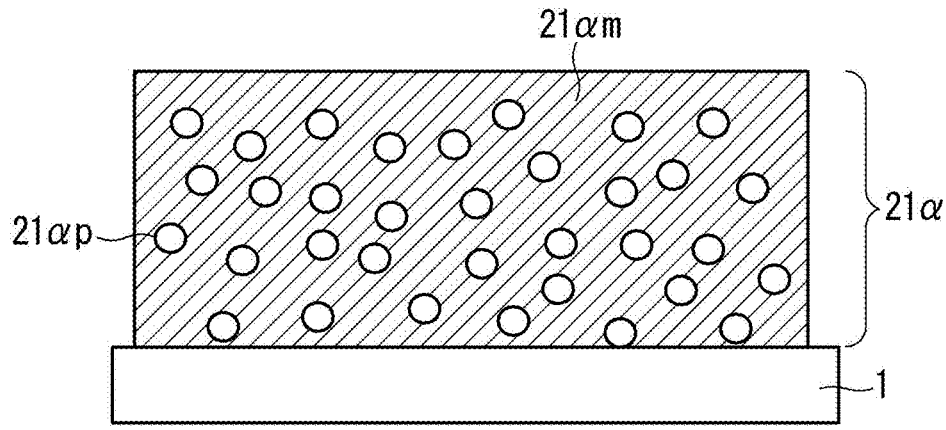
FIGS. 3A to 3C are schematic diagrams for explaining a detailed configuration of an inner leading-end protective layer 21.
Figure 3B:
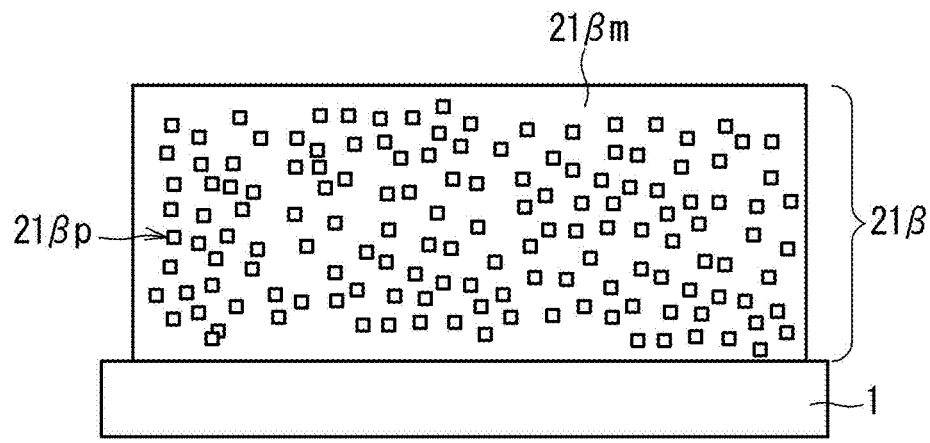
Figure 3C:
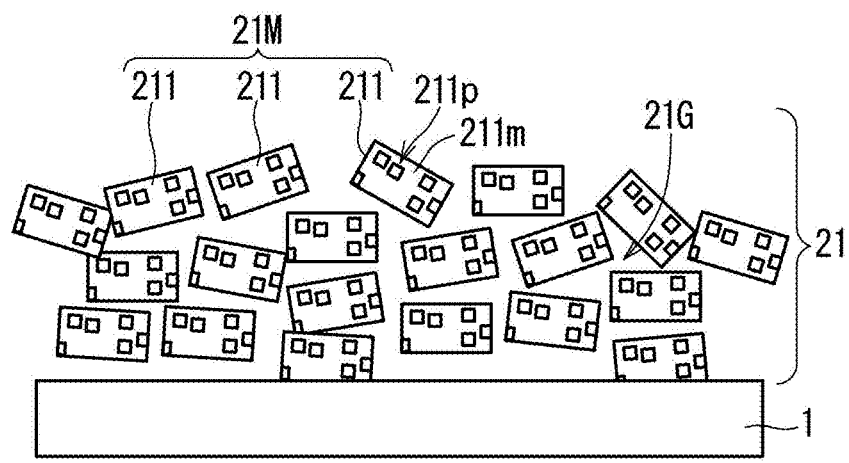

FIGS. 3A to 3C are schematic diagrams for explaining a detailed configuration of the inner leading-end protective layer 21. While the inner leading-end protective layer 21 is illustrated in FIG. 2 as a uniformly homogeneous layer for ease of illustration, the inner leading-end protective layer 21 actually has a configuration different from a conventionally known configuration. More particularly, FIG. 3C illustrates the inner leading-end protective layer 21 of the sensor element 10 according to the present embodiment, and FIGS. 3A and 3B illustrate layers different from the inner leading-end protective layer 21 for comparison.

First, FIG. 3A illustrates a case where a conventionally known typical porous ceramic layer (hereinafter, a conventional protective layer 21α) is provided, as a layer corresponding to the inner leading-end protective layer, on the element base 1.

The conventional protective layer 21α has, in a matrix region 21αm containing many dense (with substantially no voids therein) ceramic particles (e.g., alumina particles) with a micro-order particle diameter linked in three dimensions, random pores 21αp as gaps between the ceramic particles. While the individual pores 21αp discretely exist in FIG. 3A for the purpose of illustration, the pores 21αp may actually be connected in three dimensions. The conventional protective layer 21α has a thickness of approximately several hundred micrometers.

The conventional protective layer 21α is formed by attaching a slurry containing the dense ceramic particles to the surface of the element base 1 by spraying, dipping, and the like, and drying the slurry. Alternatively, firing may further be performed.

The conventional protective layer 21α can be formed to have a high porosity by attaching a slurry containing a pore-forming material vanishing through heating to the surface of the element base 1, and firing the slurry together with the element base 1 to cause the pore-forming material to vanish.

As described above, the inner leading-end protective layer 21 preferably has low thermal conductivity along the thickness thereof as it is provided to mainly suppress heat transfer from the outside to the element base 1. Thermal conductivity decreases with increasing porosity of the inner leading-end protective layer 21.

However, an allowable limit of the porosity of the conventional protective layer 21α is at most approximately 70%. The strength of the layer itself decreases with increasing porosity, and, when the porosity exceeds 70%, a sufficient strength cannot be secured, and thus water resistance cannot be secured. In the present embodiment, water resistance is expressed by a maximum amount of water not causing the water-induced breakage. In a case of the sensor element 10 including the conventional protective layer 21α as the inner leading-end protective layer, water resistance remains at most at approximately 20 μL.

Furthermore, the inner leading-end protective layer preferably has low heat capacity to reduce the heating-up time of the sensor element 10 at the start of driving of the gas sensor 100 and the like. While heat capacity of the inner leading-end protective layer tends to decrease with decreasing thickness and increasing number of voids or porosity, the porosity of the pores 21αp of the conventional protective layer 21α remains at most at approximately 70% in terms of the manufacturing process thereof. There is thus a limit on reduction of heat capacity through the increase in porosity.

Next, FIG. 3B illustrates a case where a ceramic layer having a porous structure (hereinafter, a fine porous protective layer 21β) having many fine pores 21βp with a nano-order pore diameter dispersed in a matrix region 21βm including oxide particles with a nano-order particle diameter is provided as a layer corresponding to the inner leading-end protective layer.

The matrix region 21βm includes, as a framework, $ZrO_2$ particles with a nano-order particle diameter and dissimilar material (e.g., $SiO_2$, $TiO_2$, $La_2O_3$, and $La_2Zr_2O_7$) particles existing on the surfaces of the $ZrO_2$ particles (preferably between the particles) or dissolved in the $ZrO_2$ particles and having a smaller particle diameter than the $ZrO_2$ particles as disclosed in Japanese Patent No. 6407887, for example. In this case, the fine porous protective layer 21β is formed by attaching a slurry including the $ZrO_2$ particles, the dissimilar material particles, and a pore-forming material (e.g., carbon black) with a nano-order size to the surface of the element base 1 by spraying, dipping, and the like, and firing the slurry together with the element base 1.

A maximum allowable porosity when the fine porous protective layer 21β is provided as the inner leading-end protective layer as illustrated in FIG. 3B is approximately 70% as with the maximum allowable porosity of the conventional protective layer 21α, but the fine porous protective layer 21β itself tends to have a higher strength than the conventional protective layer 21α having substantially the same porosity, due to the constitution that the fine pores 21βp are dispersed. In addition, the fine porous protective layer 21β has lower thermal conductivity than the conventional protective layer 21α as it has a smaller pore diameter, and thus the sensor element 10 including the fine porous protective layer 21β as the inner leading-end protective layer also has high water resistance. A maximum value of approximately 25 μL can thus be achieved, for example.

The fine porous protective layer 21β, however, is disadvantageous in that cracking is likely to occur during firing in terms of a manufacturing process thereof, an increase in thickness is difficult, and the thickness remains at most at approximately 100 μm. It is thus difficult to improve water resistance through the increase in thickness of the fine porous protective layer 21β. The fine porous protective layer 21β is also disadvantageous in that adhesion to the element base 1 cannot sufficiently be obtained, and the strength cannot be secured.

The inner leading-end protective layer 21 of the sensor element 10 according to the present embodiment illustrated in FIG. 3C takes into consideration the above-mentioned disadvantages of the conventional protective layer 21α and the fine porous protective layer 21β. FIG. 4 is a cross-sectional SEM image of a portion of the inner leading-end protective layer 21 and a partial high magnification image thereof.

As illustrated in FIG. 3C, the inner leading-end protective layer 21 has a configuration in which a framework structure of a matrix region 21M thereof is formed by many porous pieces 211 linked in three dimensions and voids (coarse voids) 21G as gaps between the porous pieces 211 randomly exist. In this case, the voids 21G correspond to the pores 21αp of the conventional protective layer 21α. Black regions interposed between white or gray particles with a micro-order size are observed in FIG. 4. The white or gray particles correspond to the porous pieces 211, and the black regions correspond to the voids 21G.

The porous pieces 211 have a size of approximately 10 μm to 200 μm. The inner leading-end protective layer 21 is provided to have a thickness T of 50 μm to 1000 μm, and have many voids 21G with a size of 1 μm or more in the layer due to the porous pieces.

Assume that the size of each of the voids 21G of the inner leading-end protective layer 21 is defined by a value of a maximum inscribed circle diameter of a region where the porous pieces 211 do not exist, identified by image analysis of a cross-sectional scanning electron microscope (SEM) image of the inner leading-end protective layer 21 using a known method.

The porous pieces 211 each have a matrix region 211m constituted by oxide particles with a nano-order particle diameter and many fine pores 211p with a nano-order pore diameter dispersed in the region. The porous pieces 211 can be obtained by singulating a constituent material of the fine porous protective layer 21β, for example. In this case, the fine pores 211p correspond to the fine pores 21βp of the fine porous protective layer 21β. The high magnification image on the right side of FIG. 4 shows the fine pores 211p.

In the inner leading-end protective layer 21, both the voids 21G and the fine pores 211p of the porous pieces 211 function as pores. Thus, even when the voids 21G are present in the inner leading-end protective layer 21 at substantially the same ratio as the porosity of the conventional protective layer 21α, the porosity of the inner leading-end protective layer 21 as a whole is higher than that of the conventional protective layer 21α due to the presence of the fine pores 211p. As a result, even when the inner leading-end protective layer 21 according to the present embodiment has a porosity higher than the allowable porosity of the conventional protective layer 21α or the fine porous protective layer 21α, the strength of the layer as a whole can be secured. Specifically, a maximum porosity of approximately 90% is allowable.

The sensor element 10 including the inner leading-end protective layer 21 having the structure can have water resistance of 30 μL or more, which is sufficiently higher than that of a conventional sensor element.

Furthermore, in the present embodiment, the framework structure is formed by the porous pieces 211 having high strength, so that the inner leading-end protective layer 21 can have the voids 21G with a relatively large size of approximately several hundred micrometers (at least 1 μm or more) while the strength of the layer itself is secured. In this case, heat capacity is reduced compared with a case where the conventional protective layer 21α or the fine porous protective layer 21β is provided as the inner leading-end protective layer.

Figure 5:
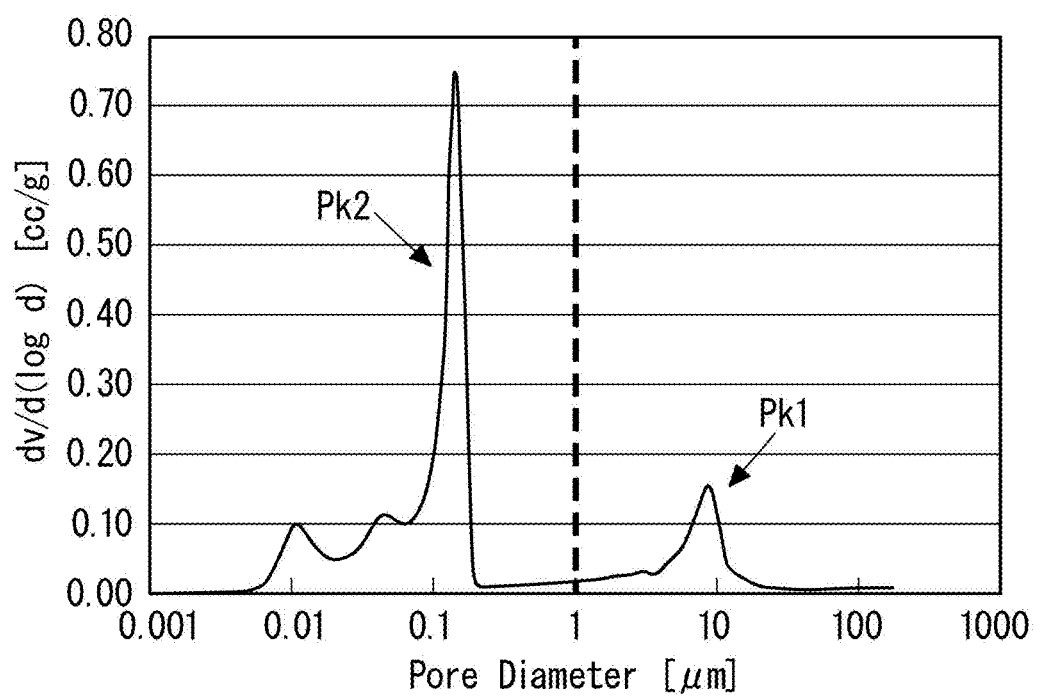
FIG. 5 shows a result of measurement of pore diameter distribution by mercury intrusion (mercury porosimetry).

FIG. 5 shows a result of measurement of pore diameter distribution by mercury intrusion (mercury porosimetry) of a test piece including a constituent material of the inner leading-end protective layer 21 prepared under certain conditions. In FIG. 5, a peak Pk1 is present at a pore diameter (Pore Diameter in FIG. 5) along a horizontal axis of a little less than 10 μm, and a maximum peak Pk2 is present at a pore diameter of approximately 0.1 μm (100 nm). Sub-peaks are also present at a pore diameter smaller than that of the peak Pk2. On the other hand, it is confirmed from FIG. 5 that there are almost no pores with a pore diameter of approximately 1 μm between the peak Pk1 and the peak Pk2.

This result suggests that, when the inner leading-end protective layer 21 has the above-mentioned configuration, pores actually existing in the layer are polarized into the voids 21G with a size of 1 μm or more and the fine pores 211p with a nano-order diameter of the porous pieces 211. That is to say, it is determined that the peak Pk1 corresponds to the voids 21G, and the peak Pk2 and the sub-peaks thereof correspond to the fine pores 211p of the porous pieces 211.

More particularly, the inner leading-end protective layer 21 actually has the voids 21G with a size varying according to formation conditions. Thus, although the peak Pk1 is present at a pore diameter of a little less than 10 μm in FIG. 5, a pore diameter providing the peak Pk1 actually varies in the inner leading-end protective layer 21. However, the voids 21G with a size of less than 1 μm are rarely formed due to manufacturing difficulties.

On the other hand, the fine pores 211p are provided to have a nano-order size as can be seen from a process of forming the porous pieces 211. The fine pores 211p with a size of more than 1 μm are thus also rarely formed.

Thus, pores with a size of 1 μm or more are the voids 21G, and pores with a size of less than 1 μm are the fine pores 211p virtually in the inner leading-end protective layer 21.

In the present embodiment, by suitably determining a manner of formation of the inner leading-end protective layer 21 including a manner of formation of the voids 21G and the fine pores 211p, water resistance of the sensor element 10 is improved, and heat capacity of the inner leading-end protective layer 21 is reduced while the strength is secured.

Specifically, the inner leading-end protective layer 21 is provided to have a porosity (an overall porosity) of 40% to 90%, and a coarse porosity corresponding to a porosity of pores with a size of 1 μm or more (substantially almost the coarse voids 21G) of 1% to 55%. In this case, the sensor element 10 has water resistance of 20 μL or more, which is at least substantially the same as or higher than that of a typical sensor element having a conventional configuration, for example, including the conventional protective layer 21α, and thermal conductivity of the inner leading-end protective layer 21 is reduced. That is to say, the sensor element 10 having high water resistance and low thermal conductivity of the inner leading-end protective layer 21 is achieved.

Assume that the porosity (overall porosity) is herein a porosity of all the pores of the inner leading-end protective layer 21 including both the fine pores 211$p$ and the voids 21G, and is obtained by mercury intrusion (mercury porosimetry). On the other hand, the coarse porosity is identified by image analysis of the cross-sectional scanning electron microscope (SEM) image of the inner leading-end protective layer 21 using the known method. The coarse porosity corresponds to the porosity of the conventional protective layer 21α. A value obtained by subtracting the coarse porosity from the overall porosity corresponds to the porosity (a fine pore porosity) of only the fine pores 211$p$ of the porous pieces 211.

The inner leading-end protective layer 21 preferably has an overall porosity of 50% to 90%. In this case, the sensor element 10 has higher water resistance of 25 µL or more while thermal conductivity of the inner leading-end protective layer 21 is reduced.

The inner leading-end protective layer 21 more preferably has an overall porosity of 60% to 90% and a coarse porosity of 10% to 55%. In this case, the sensor element 10 has extremely high water resistance of 30 µL or more while thermal conductivity of the inner leading-end protective layer 21 is reduced.

The area of contact between the inner leading-end protective layer 21 and the element base 1 is preferably 10% or more of the total area of a portion of the element base 1 surrounded by the inner leading-end protective layer 21. A portion of the inner leading-end protective layer 21 as a target of the area of contact is a portion contributing to securement of adhesion of the leading-end protective layer 2 to the element base 1, that is, a portion being in contact with the element base 1 and supporting (holding) the leading-end protective layer 2. Thus, any particles including a component of the inner leading-end protective layer 21 but only adhering to the surface of the element base 1 and not contributing to support are excluded from the target of the area of contact. Heat transfer is reduced with decreasing area of contact, but the area of contact of less than 10% is not preferable because the strength of the leading-end protective layer 2 is not secured, the leading-end protective layer 2 is likely to be damaged by the occurrence of cracking and the like when water droplets adhere while the gas sensor 100 is in use, and, in the first place, it is difficult to form the inner leading-end protective layer 21 itself.

The area of contact between the inner leading-end protective layer 21 and the element base 1 depends on a ratio at which a binder is mixed in a slurry (an inner protective layer slurry) used for formation of the inner leading-end protective layer 21 described below, the viscosity of the slurry, a drying time, a drying temperature, and an orientation of the element base 1 during drying after the element base 1 is attached to the binder by dipping and the like to form the inner leading-end protective layer 21, for example, and can be increased by increasing the ratio at which the binder is mixed, increasing the viscosity of the slurry, increasing the drying time, increasing the drying temperature, and devising the orientation of the element base 1 during drying.

A ratio of the area of contact of the inner leading-end protective layer 21 to the element base 1 can be evaluated by image analysis of the cross-sectional SEM image.

As described above, the inner leading-end protective layer 21 has a thickness T of 50 µm to 1000 µm, and has the voids 21G with a size of 1 µm or more while satisfying the overall porosity and the coarse porosity described above. The size of each of the voids 21G along the thickness naturally does not exceed the thickness T of the inner leading-end protective layer 21, and typically remains at most at 30% to 50% or less of the thickness T.

On the other hand, when the inner leading-end protective layer 21 is imaginarily bisected, along the thickness thereof, into a region closer to the surface (surface side region) and a region closer to the element base 1 (base side region), the voids 21G are more likely to be formed in the base side region than in the surface side region as the overall porosity and the coarse porosity increase.

Figure 6:
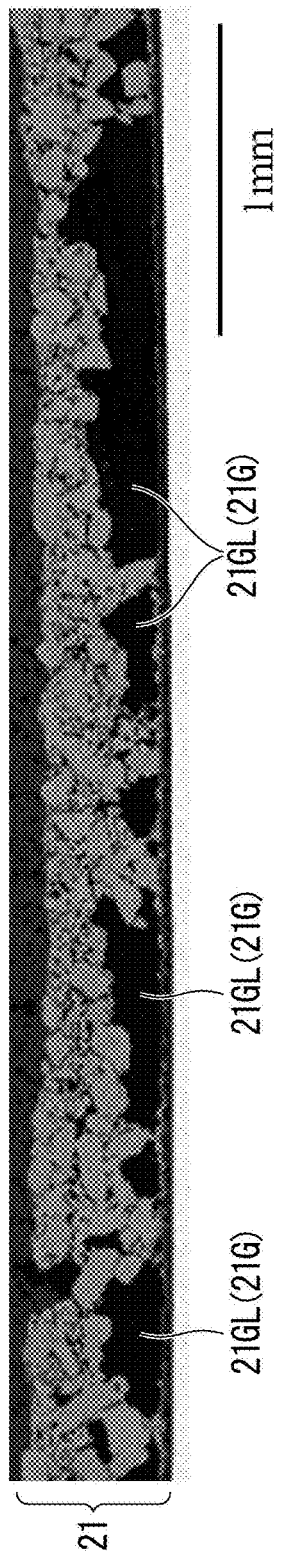
FIG. 6 is an SEM image showing an inner leading-end protective layer 21 having layer-like voids 21G formed prominently.
Figure 7:
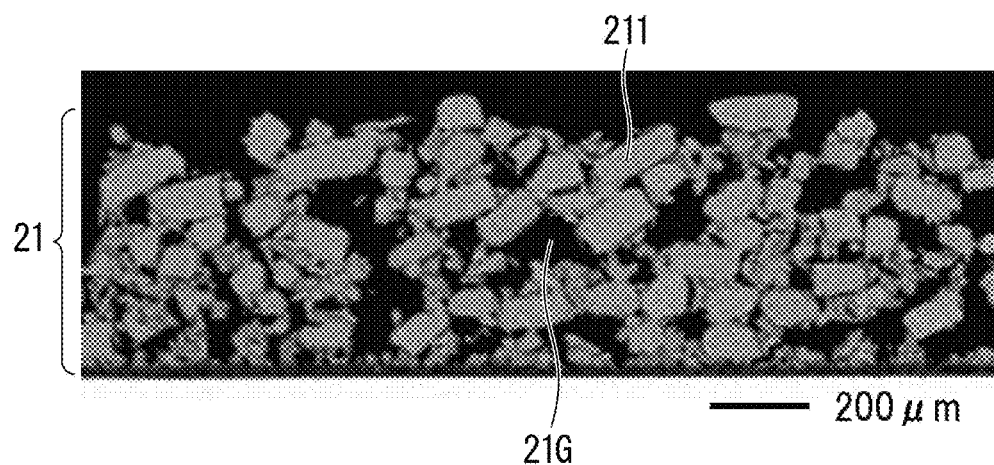
FIG. 7 is an SEM image showing an inner leading-end protective layer having voids 21G with a maximum size substantially the same as a maximum size of porous pieces 211.

When the tendency becomes prominent, the voids 21G are formed to be in the form of layers along the surface of the element base 1. FIG. 6 is an SEM image showing the inner leading-end protective layer 21 having such layer-like voids 21G formed prominently. FIG. 7 is an SEM image showing the inner leading-end protective layer having voids 21G with a maximum size remaining at a value substantially the same as a value of a maximum size of each of the porous pieces 211 for contrast. In a case of the inner leading-end protective layer 21 shown in FIG. 7, the porous pieces 211 have a maximum size of approximately 200 µm, and the voids 21G have substantially the same maximum size. In contrast, in a case of the inner leading-end protective layer 21 shown in FIG. 6, layer-like voids 21G having substantially half the height (thickness) of the layer, but having a size along the surface of the element base 1 (a left to right direction in FIG. 6) of several hundred micrometers to one millimeter or more, which is much larger than the size of the porous pieces 211, exist in a lower half in FIG. 6 of the inner leading-end protective layer 21 closer to the element base 1. Such voids 21G are hereinafter particularly referred to as large layer-like voids 21GL.

When the voids 21G exist locally in the base side region of the inner leading-end protective layer 21 as described above, a coarse porosity ratio x2/x1 is greater than one, where x1 is a surface side coarse porosity as the coarse porosity only in the surface side region, x2 is a base side coarse porosity as the coarse porosity only in the base side region. The coarse porosity ratio x2/x1 more greatly exceeds one as formation of the large layer-like voids 21GL is prominent.

For confirmation, the surface side coarse porosity x1 and the base side coarse porosity x2 are each a ratio of the area occupied by the voids 21G to a total area of the target region in the cross-sectional SEM image of the inner leading-end protective layer 21. Thus, when an inequality x2/x1>1 is satisfied, the base side coarse porosity x2 may exceed the coarse porosity of the inner leading-end protective layer 21 as a whole. The coarse porosity of the inner leading-end protective layer 21 as a whole is hereinafter also particularly referred to as an overall coarse porosity for differentiation.

When the inequality x2/x1>1 is satisfied, and thus the large layer-like voids 21GL as shown in FIG. 6 are formed, portions of the inner leading-end protective layer 21 being in contact with the element base 1 and supporting the leading-end protective layer 2 are reduced, and discretely exist, and, as a result, the area of contact between the inner leading-end protective layer 21 and the element base 1 is reduced. This is preferable in terms of securement of thermal insulating properties (reduction in heat transfer) and, further, improvement in water resistance of the sensor element 10. In particular, when an inequality x2/x1≥2.4 is satisfied, extremely high water resistance is achieved.

The inner leading-end protective layer 21 preferably has a thickness T of 400 μm to 1000 μm, and more preferably has a thickness T of 500 μm to 1000 μm.

Process of Manufacturing Sensor Element

Figure 8:
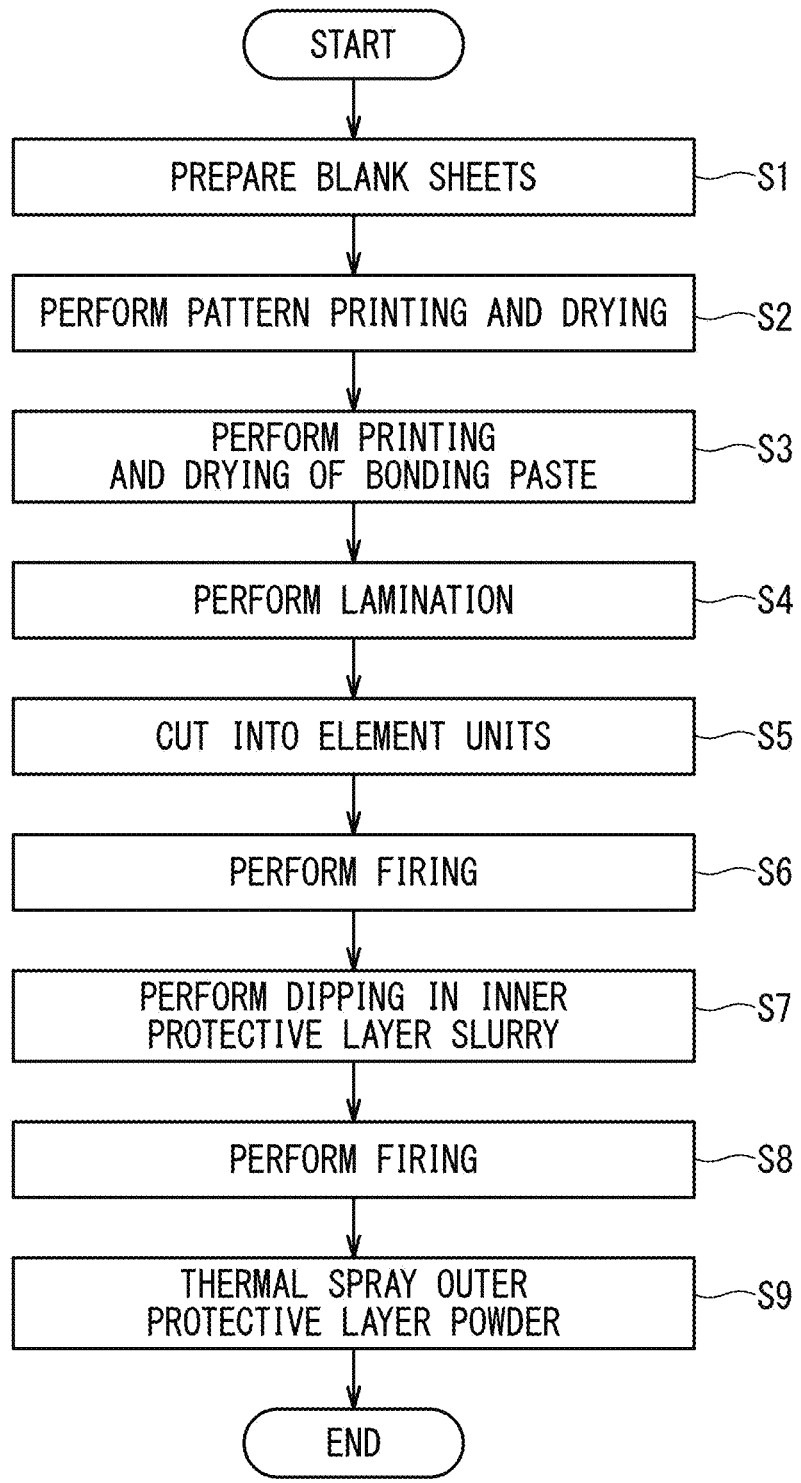
FIG. 8 is a flowchart of processing at the manufacture of the sensor element 10.

One example of a process of manufacturing the sensor element 10 having a configuration and features as described above will be described next. FIG. 8 is a flowchart of processing at the manufacture of the sensor element 10.

The element base 1 is manufactured first. At the manufacture of the element base 1, a plurality of blank sheets (not illustrated) being green sheets containing the oxygen-ion conductive solid electrolyte, such as zirconia, as a ceramic component and having no pattern formed thereon are prepared first (step S1).

The blank sheets have a plurality of sheet holes used for positioning in printing and lamination. The sheet holes are formed to the blank sheets in advance prior to pattern formation through, for example, punching by a punching machine. Green sheets corresponding to a portion of the ceramic body 101 in which an internal space is formed also include penetrating portions corresponding to the internal space formed in advance through, for example, punching as described above. The blank sheets are not required to have the same thickness, and may have different thicknesses in accordance with corresponding portions of the element base 1 eventually formed.

After preparation of the blank sheets corresponding to the respective layers, pattern printing and drying are performed on the individual blank sheets (step S2). Specifically, a pattern of various electrodes, a pattern of the heater 150 and the insulating layer 151, a pattern of the electrode terminals 160, a pattern of the main surface protective layers 170, a pattern of internal wiring, which is not illustrated, and the like are formed. Application or placement of a sublimable material (vanishing material) for forming the first diffusion control part 110, the second diffusion control part 120, the third diffusion control part 130, and the fourth diffusion control part 140 is also performed at the time of pattern printing.

The patterns are printed by applying pastes for pattern formation prepared in accordance with the properties required for respective formation targets onto the blank sheets using known screen printing technology.

After pattern printing on each of the blank sheets, printing and drying of a bonding paste are performed to laminate and bond the green sheets (step S3). The known screen printing technology can be used for printing of the bonding paste, and the known drying means can be used for drying after printing.

The green sheets to which an adhesive has been applied are then stacked in a predetermined order, and the stacked green sheets are crimped under predetermined temperature and pressure conditions to thereby form a laminated body (step S4). Specifically, crimping is performed by stacking and holding the green sheets as a target of lamination on a predetermined lamination jig, which is not illustrated, while positioning the green sheets at the sheet holes, and then heating and pressurizing the green sheets together with the lamination jig using a lamination machine, such as a known hydraulic pressing machine. The pressure, temperature, and time for heating and pressurizing depend on a lamination machine to be used, and these conditions may be determined appropriately to achieve good lamination.

After the laminated body is obtained as described above, the laminated body is cut out at a plurality of positions to obtain unit bodies eventually becoming the individual element bases 1 (step S5).

The unit bodies as obtained are then each fired at a firing temperature of approximately 1300° C. to 1500° C. (step S6). The element base 1 is thereby manufactured. That is to say, the element base 1 is generated by integrally firing the ceramic body 101 made of the solid electrolyte, the electrodes, and the main surface protective layers 170. Integral firing is performed in this manner, so that the electrodes each have sufficient adhesion strength in the element base 1.

After the element base 1 is manufactured by the above-mentioned procedures, the inner leading-end protective layer 21 and the outer leading-end protective layer 22 are formed with respect to the element base 1.

The inner leading-end protective layer 21 is formed using a slurry for forming the inner leading-end protective layer containing the porous pieces 211 (the inner protective layer slurry) prepared in advance.

Figure 9:
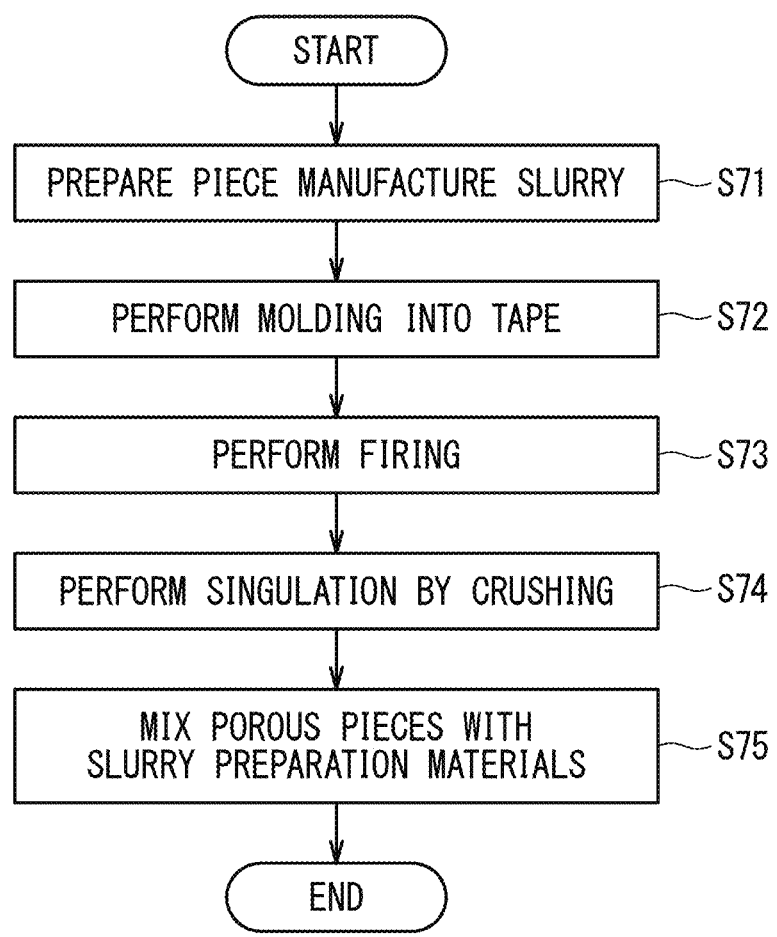
FIG. 9 is a flowchart of processing at the manufacture of an inner protective layer slurry.

FIG. 9 is a flowchart of processing at the manufacture of the inner protective layer slurry. At the manufacture of the inner protective layer slurry, the $ZrO_2$ particles with a nano-order particle diameter, the dissimilar material (e.g., $SiO_2$, $TiO_2$, $La_2O_3$, and $La_2Zr_2O_7$) particles with a smaller particle diameter than the $ZrO_2$ particles, the pore-forming material (e.g., carbon black) with a nano-order size, a predetermined binder, a plasticizer, a solvent, and the like are first mixed at a ratio corresponding to a desired value of the fine pore porosity to manufacture a piece manufacture slurry (step S71).

The piece manufacture slurry is molded into the form of a tape having a thickness of approximately 50 μm to 200 μm (step S72), and a mold as obtained is fired at a temperature of approximately 1000° C. to 1200° C. (step S73). A fired body as obtained is crushed (disintegrated) using a predetermined crushing (disintegration) means to obtain numerous porous pieces 211 having a size of approximately 10 μm to 200 μm and having many nano-order fine pores (step S74). As shown in FIG. 4, the porous pieces 211 each do not have a particularly limited shape, and may have various shapes, such as a spherical shape and a planar shape.

The porous pieces 211, the predetermined binder, the plasticizer, the solvent, and the like are mixed at a ratio corresponding to a desired value of the coarse porosity to obtain the inner protective layer slurry (step S75). A ceramic material different from the porous pieces 211 may further be mixed in the inner protective layer slurry.

The inner leading-end protective layer 21 is formed by dipping (immersing) the element base 1 in the inner protective layer slurry manufactured in advance by such procedures (step S7), attaching the inner protective layer slurry in a range of formation of the inner leading-end protective layer of the element base 1 so that the inner protective layer slurry has a predetermined thickness, and then firing, after drying for a predetermined time, the inner protective layer slurry at a temperature of approximately 800° C. to 900° C. (step S8).

When the inner leading-end protective layer 21 is provided in this manner, the voids 21G are more likely to be formed in a portion closer to the element base 1 than in a portion in the vicinity of an outer periphery. Such a tendency is observed in the cross-sectional SEM image of the inner leading-end protective layer 21 shown in FIG. 4. This is because, during drying after attachment of the inner protective layer slurry, drying of the slurry and, further, generation of an organic component gas progress from a side of the outer periphery, and thus the organic component gas generated in the portion closer to the element base 1 is less likely to be desorbed to the outside, and, as a result, coarse bubbles are formed in the layer. This is also the reason why the layer-like voids 21G and, further, the large layer-like voids 21GL are more likely to be formed as the overall porosity and the coarse porosity increase as described above.

Upon formation of the inner leading-end protective layer 21, powder (e.g., alumina powder) for forming the outer leading-end protective layer similarly prepared in advance is thermal sprayed at a position of the element base 1 as a target of formation of the outer leading-end protective layer 22 to have an intended thickness (step S9) to thereby form the outer leading-end protective layer 22 having a desired porosity. The alumina powder for forming the outer leading-end protective layer does not contain the pore-forming material. Known technology is also applicable to the thermal spraying. Alternatively, the outer leading-end protective layer 22 may be formed through dipping (immersion) in an outer protective layer slurry prepared in advance as with the inner leading-end protective layer 21.

The sensor element 10 is obtained by the above-mentioned procedures. The sensor element 10 thus obtained is housed in a predetermined housing, and built into the main body (not illustrated) of the gas sensor 100.

As described above, according to the present embodiment, the inner leading-end protective layer having a configuration in which the matrix region is formed by the many porous pieces each having many fine pores and the voids as the gaps between the porous pieces randomly exist therein is used as one of the leading-end protective layers for protecting a portion of the element base of the sensor element in which the temperature becomes high when the sensor element is in use, so that the sensor element can have water resistance of 30 µL or more, which is sufficiently higher than that of the conventional sensor element, and heat capacity of the inner leading-end protective layer can be reduced while the strength of the layer itself is secured.

Modifications

The above-mentioned embodiment is targeted at a sensor element having three internal chambers, but the sensor element is not necessarily required to have a three-chamber structure. That is to say, the sensor element may have one internal chamber or two internal chambers.

In the above-mentioned embodiment, the inner leading-end protective layer 21 is provided directly to the element base 1 through dipping in the inner protective layer slurry, but the inner leading-end protective layer 21 may not necessarily be provided directly to the element base 1 through dipping. For example, the inner leading-end protective layer 21 may be provided by covering the element base 1 with the inner leading-end protective layer 21 formed in the form of a cap in advance, and fixing (securing) the inner leading-end protective layer 21 to the element base 1. In this case, the inner leading-end protective layer 21 in the form of the cap can be manufactured by preparing an element dummy (a dummy rod) having a similar shape to the element base 1 and made of resin, forming a slurry film on an outer periphery of the dummy rod through dipping of the element dummy in the inner protective layer slurry, and then firing the slurry film together with the element dummy to burn off the element dummy. Also in this case, the outer leading-end protective layer 22 can be formed in a similar manner to that in the above-mentioned embodiment.

As shown in the above-mentioned embodiment, the configuration in which the voids 21G satisfy the relationship x2/x1>1, and, further, the configuration in which the voids 21G are formed to be in the form of the layers along the element base 1 are preferable in terms of securement of thermal insulating properties (reduction in heat transfer) and, further, improvement in water resistance of the sensor element 10. In light of the foregoing, a layer-like space may intentionally be provided between the element base 1 and the leading-end protective layer 2.

Figure 10:
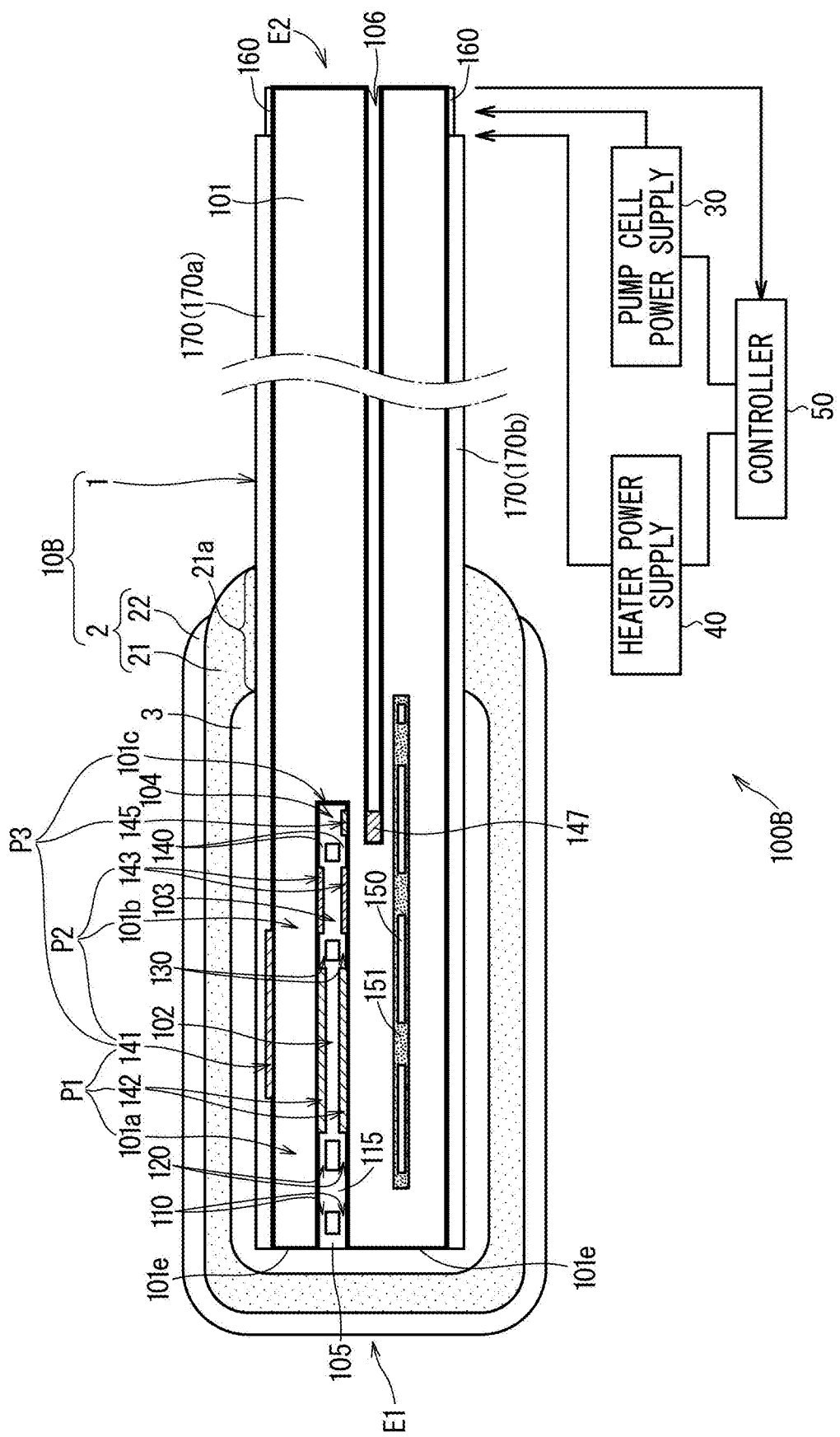
FIG. 10 is a schematic view illustrating a configuration of a gas sensor 100B according to a modification.

FIG. 10 is a schematic view illustrating a gas sensor 100B according to a modification having such a configuration. FIG. 10 includes a cross-sectional view taken along a longitudinal direction of a sensor element 10B. The gas sensor 100B has the same configuration as the gas sensor 100 except that the sensor element 10B has a configuration partially different from that of the sensor element 10.

Specifically, the sensor element 10B has in common with the sensor element 10 that both include the leading-end protective layer 2 provided to the one end portion of the element base 1 and having the laminated structure of the inner leading-end protective layer 21 and the outer leading-end protective layer 22, but differs from the sensor element 10 in that the inner leading-end protective layer 21 and the element base 1 are spaced from each other in the one end portion E1 of the element base 1 and throughout a predetermined range in the longitudinal direction of the element from the one end portion E1 on the side surfaces, and a layer-like internal space 3 is formed between them. The inner leading-end protective layer 21 is connected to the element base 1 only by a connection portion 21α provided on the side of the other end portion E2 in a range of formation of the inner leading-end protective layer 21 in the longitudinal direction of the element.

In this case, a thermally insulating space is formed in the majority of an inside of the inner leading-end protective layer 21, so that the sensor element having extremely high water resistance is achieved.

In a case of the sensor element 10B, a requirement that the area of contact between the inner leading-end protective layer 21 and the element base 1 is 10% or more of the total area of the portion of the element base 1 surrounded by the inner leading-end protective layer 21 is only required to be met by the connection portion 21α.

Various methods are applicable to formation of the internal space 3. For example, the internal space 3 can be formed by applying a sublimable material to a portion on the surface of the element base 1 as a target of formation of the internal space 3 in advance prior to formation of the inner leading-end protective layer 21 through dipping of the element base 1 in the inner protective layer slurry, and causing the sublimable material to vanish at firing thereafter. Alternatively, a leading end of the element dummy may be widened by the size of the internal space 3 at formation of the inner leading-end protective layer 21 in the form of the cap described above.

EXAMPLES

Example 1

The effect of the configuration of the inner leading-end protective layer 21 on water resistance of the sensor element 10 was evaluated. Twelve types of sensor elements 10 (Samples Nos. 1-1 to 1-12) having different combinations of the overall porosity and the coarse porosity of the inner leading-end protective layer 21 were manufactured as samples, and, after a state of formation of the leading-end protective layer 2 was observed by X-ray CT, a water resistance test was conducted on each of sensor elements 10 having no problem with the state of formation.

The inner leading-end protective layer 21 had a thickness T of 500 μm, and the fine pores 211$p$ of the porous pieces 211 had a pore diameter of 10 nm or more and less than 1 μm.

The outer leading-end protective layer 22 was made of alumina, and had a porosity of 30% and a thickness of 200 μm.

Seven types of sensor elements (Samples Nos. 2-1 to 2-7) having different porosities and each including the conventional protective layer 21α in place of the inner leading-end protective layer 21 were also manufactured for comparison, and were similarly evaluated.

The ceramic particles forming the conventional protective layer 21α have no fine pores, and the pores 21α$p$ correspond to the voids 21G of the inner leading-end protective layer 21, so that the conventional protective layer 21α can imaginarily be considered as the inner leading-end protective layer 21 having the matrix region 21M formed by the porous pieces 211 with a fine pore porosity of 0%, and having the overall porosity matching the coarse porosity.

The conventional protective layer 21α had a thickness of 500 μm, and the pores 21α$p$ had a pore diameter of 1 μm to 50 μm.

Water resistance was evaluated by applying water droplets of 0.1 μL, at a time to a side of the pump surface of each of the sensor elements 10 while a pump current in the main pump cell P1 was measured with the sensor element 10 being heated to approximately 500° C. to 900° C. by the heater 150, and setting a maximum amount of water not causing an abnormal measurement output to an index value of water resistance.

The presence or absence of the fine pores of the pieces, the overall porosity, the coarse porosity, the state of formation of the inner leading-end protective layer 21, and a result of evaluation of water resistance of each of the samples are shown in Table 1 as a list.

In a case where the conventional protective layer 21α is provided as the inner leading-end protective layer 21, the overall porosity corresponds to the coarse porosity as described above, so that the same numerical value as that in an "OVERALL POROSITY" column is shown in parentheses in a "COARSE POROSITY" column in each of Samples Nos. 2-1 to 2-7 in Table 1.

In a "LAYER FORMATION STATE" column, a circle is marked for each of samples in which there was no problem with formation of the inner leading-end protective layer 21, and a cross is marked for a sample in which the inner leading-end protective layer 21 could not be formed or the inner leading-end protective layer 21 as formed was cracked.

Specifically, in each of samples other than Samples Nos. 1-12, 2-6, and 2-7, no particular problem with formation of the inner leading-end protective layer 21 was found.

More particularly, there was no problem with formation of the inner leading-end protective layer 21 only in each of samples in which the overall porosity was 70% or less in a case where the conventional protective layer 21α not containing the porous pieces 211 was provided as the inner leading-end protective layer 21, whereas the inner leading-end protective layer 21 was formed without any problem when the overall porosity was 90% or less in a case where the inner leading-end protective layer 21 is provided to contain the porous pieces 211. This result suggests that the strength of the inner leading-end protective layer 21 can be secured by using the porous pieces 211 even when the overall porosity is high.

On the other hand, as for evaluation of water resistance, each of samples in which water resistance was 30 μL or more was evaluated to have extremely high water resistance, and a double circle is marked for the sample in a "WATER RESISTANCE" column. Each of samples in which water resistance was 25 μL or more and less than 30 μL was evaluated to have high water resistance, and a circle is marked for the sample in the "WATER RESISTANCE" column. Each of samples in which water resistance was 20 μL or more and less than 25 μL was evaluated to have substantially the same water resistance as a conventionally known typical sensor element 10, and a triangle is marked for the sample. A cross is marked for a sample which was applied to none of the evaluations and in which water resistance was less than 20 μL.

TABLE 1

| SAMPLE No. | PRESENCE OR ABSENCE OF FINE PORES OF PIECES | OVERALL POROSITY (%) | COARSE POROSITY (%) | LAYER FORMATON STATE | WATER RESISTANCE |
|---|---|---|---|---|---|
| 1-1 | PRESENT | 50 | 1 | ○ | ○ |
| 1-2 | | 65 | 1 | ○ | ○ |
| 1-3 | | 67 | 5 | ○ | ○ |
| 1-4 | | 69 | 10 | ○ | ◎ |
| 1-5 | | 60 | 20 | ○ | ◎ |
| 1-6 | | 74 | 25 | ○ | ◎ |
| 1-7 | | 76 | 30 | ○ | ◎ |
| 1-8 | | 79 | 40 | ○ | ◎ |
| 1-9 | | 81 | 45 | ○ | ◎ |
| 1-10 | | 85 | 50 | ○ | ◎ |
| 1-11 | | 90 | 55 | ○ | ◎ |
| 1-12 | | 95 | 60 | X | — |
| 2-1 | ABSENT | 30 | (30) | ○ | X |
| 2-2 | | 40 | (40) | ○ | Δ |
| 2-3 | | 50 | (50) | ○ | Δ |
| 2-4 | | 60 | (60) | ○ | ○ |
| 2-5 | | 70 | (70) | ○ | ○ |
| 2-6 | | 75 | (75) | X | — |
| 2-7 | | 80 | (80) | X | — |

It can be seen from Table 1 that, in a case where the conventional protective layer 21α containing the ceramic particles not having the fine pores 211p was used, high water resistance of 25 μL or more was obtained only when the overall porosity, which corresponds to the coarse porosity, was 60% to 70% close to a manufacturing limit, whereas, in a case where the inner leading-end protective layer 21 is provided to contain the porous pieces 211, high water resistance of 25 μL or more was achieved when the overall porosity was 50% to 90% even if the coarse porosity was 1% to 55%. It can also be seen that, water resistance in each of the samples in which these ranges were satisfied was higher than that in a case where the conventional protective layer 21α was provided to have the overall porosity, which corresponds to the coarse porosity, substantially the same as the coarse porosity of the sample. Viewed another way, this indicates that high water resistance is achieved by securing the fine pore porosity using the porous pieces 211 to increase the overall porosity, even when the coarse porosity is low.

It is further indicated that extremely high water resistance of 30 μL or more is achieved in a case where the inner leading-end protective layer 21 is provided to have an overall porosity of 60% to 90% and a coarse porosity of 10% to 55%.

Example 2

The effect of the configuration of the inner leading-end protective layer 21 on heat capacity was evaluated. Evaluation samples (Samples Nos. 1-13 and 1-14) mimicking two types of inner leading-end protective layers 21 having different combinations of the overall porosity and the coarse porosity were manufactured as samples, and density (apparent density) and heat capacity thereof were evaluated. Specifically, a sample for density measurement having a diameter of 10 mm and a thickness of 1 mm and a sample for specific heat measurement having a diameter of 5 mm and a thickness of 1 mm were manufactured by drying respective inner protective layer slurries under the same conditions as those at the manufacture of the sensor element 10, and further degreasing and firing the dried inner protective layer slurries. The fine pores 211p of the porous pieces 211 had a pore diameter of 10 nm or more and less than 1 μm. Sample No. 1-13 was manufactured under generally the same conditions as those for the inner leading-end protective layer 21 of Sample No. 1-2 in Example 1.

Two types of evaluation samples (Samples Nos. 2-8 and 2-9) mimicking the conventional protective layer 21α and having different porosities were also manufactured for comparison, and were similarly evaluated. The samples each had sizes similar to the above-mentioned sizes. Sample No. 2-8 was manufactured under the same conditions as those for the conventional protective layer 21α of Sample No. 2-3. The pores 21αp had a pore diameter of 1 μm to 20 μm.

Density was evaluated by mercury porosimetry.

Heat capacity was evaluated by measuring specific heat by DSC, and converting the measured specific heat into heat capacity by taking a film volume into consideration.

The presence or absence of the fine pores of the pieces, the overall porosity, the coarse porosity, and results of evaluation of density and heat capacity of each of the samples are shown in Table 2 as a list.

TABLE 2

| SAMPLE No. | PRESENCE OR ABSENCE OF FINE PORES OF PIECES | OVERALL POROSITY (%) | COARSE POROSITY (%) | DENSITY (g/cm$^3$) | HEAT CAPACITY (kJ/m$^3$ · K) |
|---|---|---|---|---|---|
| 1-13 | PRESENT | 62 | 1 | 1.86 | 890 |
| 1-14 |  | 58 | 40 | 1.19 | 570 |
| 2-8 (=2-3) | ABSENT | 50 | (50) | 1.56 | 1160 |
| 2-9 |  | 56 | (56) | 1.18 | 840 |

As shown in Table 2, as for the samples in each of which the conventional protective layer 21α was provided, density and heat capacity were lower in Sample No. 2-9 in which the overall porosity, which corresponds to the coarse porosity, was higher than in Sample No. 2-8.

In contrast, as for the samples in each of which the inner leading-end protective layer 21 was provided to contain the porous pieces 211, heat capacity of 890 kJ/m$^3$·K, which is close to heat capacity of 840 kJ/m$^3$·K in Sample No. 2-9 in which the overall porosity was 56%, could be obtained even in Sample No. 1-13 in which the coarse porosity was only 1%. In Sample No. 1-14 in which the coarse porosity was increased to 40%, extremely low heat capacity of 570 kJ/m$^3$·K could be obtained even though the overall porosity was lower than that in Sample No. 1-13 by 4%.

This result indicates that, in a case where the inner leading-end protective layer 21 is provided to contain the porous pieces 211, heat capacity and, further, thermal conductivity of the inner leading-end protective layer 21 can be reduced with the strength secured by increasing the coarse porosity while the overall porosity is suppressed. This result further indicates that, in a case where the conventional protective layer 21α is used, heat capacity can be reduced by increasing the overall porosity, but the effect thereof is limited compared with a case where the inner leading-end protective layer 21 is provided to contain the porous pieces 211.

Example 3

The effect of a ratio of the area of contact of the inner leading-end protective layer 21 with the element base 1 on the strength of the leading-end protective layer 2 was evaluated. Four types of sensor elements 10 (Samples Nos. 1-15 to 1-18) having different ratios of the area of contact of the inner leading-end protective layer 21 with the element base 1 were manufacture as samples, and, for each of the sensor elements 10, the ratio of the area of contact with the element base 1 was evaluated, and the presence or absence of a defect (typically, a crack) of the leading-end protective layer 2 was checked through visual inspection by microscopy.

The inner leading-end protective layer 21 had a thickness T of 500 μm, and the fine pores 211p of the porous pieces 211 had a pore diameter of 10 nm or more and less than 1 μm. The overall porosity was 80%, and the coarse porosity was 45%. Samples Nos. 1-15 to 1-18 were manufactured under generally the same conditions as those for Sample No. 1-9 in Example 1.

The ratio of the area of contact and a result of observation of the presence or absence of the defect of the leading-end protective layer 2 of each of the samples are shown in Table 3 as a list.

TABLE 3

| SAMPLE No. | RATIO OF AREA OF CONTACT WITH ELEMENT BASE (%) | PRESENCE OR ABSENCE OF DEFECT |
|---|---|---|
| 1-15 | 5 | PRESENT |
| 1-16 | 10 | ABSENT |
| 1-17 | 20 | ABSENT |
| 1-18 | 30 | ABSENT |

As can be seen from Table 3, the occurrence of the defect was observed only in Sample No. 1-15 in which the ratio of the area of contact was 5%. The occurrence of the defect was not observed in each of Samples No. 1-16 to 1-18 in which the ratio of the area of contact was 10% or more.

This result indicates that the inner leading-end protective layer 21 is less likely to be damaged when the ratio of the area of contact of the inner leading-end protective layer 21 with the element base 1 is 10% or more.

Example 4

The effect of a difference in thickness of the inner leading-end protective layer 21 on water resistance was evaluated. Twelve types of sensor elements 10 (Samples Nos. 1-19 to 1-30) having different thicknesses T of the inner leading-end protective layer 21 were manufactured as samples, and the water resistance test was conducted on each of the sensor elements 10 by a similar method to that in Example 1.

The thickness T of the inner leading-end protective layer 21 was varied from 10 μm to 1000 μm. The fine pores 211$p$ of the porous pieces 211 of the inner leading-end protective layer 21 had a pore diameter of 10 nm or more and less than 1 μm. On the other hand, the overall porosity was 76%, and the coarse porosity was 36% in each of the samples. Sample No. 1-25 was manufactured under the same conditions as those for Sample No. 1-7 in Example 1.

The thickness T of the inner leading-end protective layer 21 and a result of evaluation of water resistance of each of the samples are shown in Table 4 as a list. Evaluation criteria for water resistance were similar to those in Example 1.

TABLE 4

| SAMPLE No. | THICKNESS OF INNER LEADING-END PROTECTIVE LAYER (μm) | WATER RESISTANCE |
|---|---|---|
| 1-19 | 10 | X |
| 1-20 | 50 | Δ |
| 1-21 | 100 | Δ |
| 1-22 | 200 | Δ |
| 1-23 | 300 | Δ |
| 1-24 | 400 | ○ |
| 1-25 (=1-7) | 500 | ⊚ |

TABLE 4-continued

| SAMPLE No. | THICKNESS OF INNER LEADING-END PROTECTIVE LAYER (μm) | WATER RESISTANCE |
|---|---|---|
| 1-26 | 600 | ⊚ |
| 1-27 | 700 | ⊚ |
| 1-28 | 800 | ⊚ |
| 1-29 | 900 | ⊚ |
| 1-30 | 1000 | ⊚ |

As can be seen from Table 4, water resistance was 20 μL or more in each of samples in which the inner leading-end protective layer 21 had a thickness T of 50 μm or more. In particular, water resistance was 25 μL or more in each of samples in which the inner leading-end protective layer 21 had a thickness T of 400 μm or more. Furthermore, water resistance was 30 μL or more in each of samples in which the inner leading-end protective layer 21 had a thickness T of 500 μm or more.

This result indicates that, in a case where the inner leading-end protective layer 21 is provided to contain the porous pieces 211, high water resistance can be obtained when the thickness T is 400 μm or more, and extremely high water resistance can be obtained when the thickness T is 500 μm or more.

Example 5

The effect of a difference in coarse porosity ratio $x2/x1$ on water resistance was evaluated. Five types of sensor elements 10 (Samples Nos. 1-31 to 1-35) having substantially the same overall coarse porosity but having different coarse porosity ratios $x2/x1$ were manufactured as samples, and the water resistance test was conducted on each of the sensor elements 10 by a similar method to that in Example 1.

The inner leading-end protective layer 21 had a thickness T of 500 μm in each of the samples. The fine pores 211$p$ of the porous pieces 211 of the inner leading-end protective layer 21 had a pore diameter of 10 nm or more and less than 1 μm.

Figure 11:
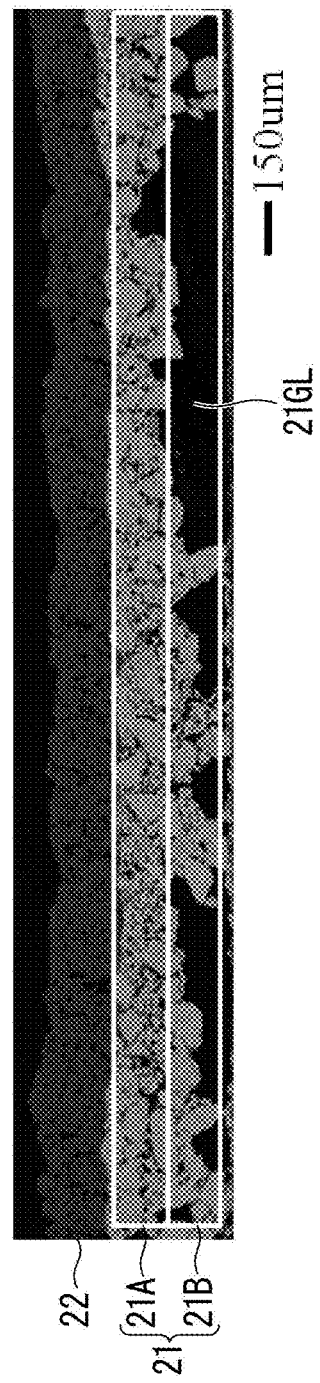
FIG. 11 is a cross-sectional SEM image of the inner leading-end protective layer 21 in Sample No. 1-33.

FIG. 11 is a cross-sectional SEM image of the inner leading-end protective layer 21 in Sample No. 1-33. The presence of the large layer-like voids 21GL in a base side region 21B is observed in FIG. 11.

FIG. 11 also shows a surface side region 21A and the base side region 21B of the inner leading-end protective layer 21 used when the surface side coarse porosity $x1$ and the base side coarse porosity $x2$ are obtained. The widest possible cross-sectional SEM image of the inner leading-end protective layer 21 as shown in FIG. 11 is obtained when the surface side coarse porosity $x1$ and the base side coarse porosity $x2$ are specifically identified to obtain the coarse porosity ratio $x2/x1$. The surface side region 21A and the base side region 21B are identified by identifying a rectangular range including substantially all of a range of formation of the inner leading-end protective layer 21, and bisecting the rectangular range along the thickness of the element. The surface side coarse porosity $x1$ and the base side coarse porosity $x2$ are obtained for the respective identified regions.

The overall coarse porosity, the surface side coarse porosity $x1$, the base side coarse porosity $x2$, the coarse porosity ratio $x2/x1$, and a result of evaluation of water resistance of each of the samples are shown in Table 5 as a list.

TABLE 5

| SAMPLE No. | COARSE POROSITY (%) | SURFACE SIDE COARSE POROSITY x1 (%) | BASE SIDE COARSE POROSITY x2 (%) | COARSE POROSITY RATIO x2/x1 | WATER RESISTANCE (μL) |
|---|---|---|---|---|---|
| 1-31 | 38 | 39 | 37 | 0.95 | 26 |
| 1-32 | 42 | 25 | 59 | 2.4 | 35 |
| 1-33 | 41 | 20 | 61 | 3.1 | 32 |
| 1-34 | 40 | 18 | 62 | 3.4 | 38 |
| 1-35 | 42 | 15 | 69 | 4.6 | 45 |

As can be seen from Table 5, while sufficiently high water resistance of 26 μL was obtained in a sample in which x2/x1 was approximately one (Sample No. 1-31), extremely high water resistance of 32 μL or more was obtained in each of samples in which x2/x1 was greater than one, more specifically, x2/x1 was 2.4 or more (Samples Nos. 1-32 to 1-35), although there was little difference in overall coarse porosity from Sample No. 1-31.

This result indicates that extremely high water resistance can be obtained by providing the inner leading-end protective layer 21 so that more voids 21G are formed in the base side region than in the surface side region to have the coarse porosity ratio x2/x1 greater than one, and, further, the large layer-like voids 21GL are formed, and preferably by providing the inner leading-end protective layer 21 so that an inequality x2/x1>2.4 is satisfied.

What is claimed is:

1. A sensor element of a gas sensor, the sensor element comprising:
    an element base being a ceramic structured body having a gas inlet in one end portion thereof and including therein a gas distribution part communicating from said gas inlet in a longitudinal direction, a measurement gas containing a gas component to be measured being introduced into said gas distribution part through said gas inlet, said gas component to be measured being sensed by a sensing part disposed in said gas distribution part; and
    a leading-end protective layer disposed around an outer periphery of said element base in a predetermined range from said one end portion, wherein
    said leading-end protective layer has a laminated structure of:
        an inner leading-end protective layer having coarse voids with a size of 1 μm or more in a matrix region having a framework structure formed by porous pieces each having fine pores with a pore diameter of 10 nm or more and less than 1 μm; and
        an outer leading-end protective layer disposed to cover said inner leading-end protective layer, and having a lower porosity than said inner leading-end protective layer, and
    said inner leading-end protective layer has:
        an overall porosity of 40% or more and 90% or less; and
        a coarse porosity of 1% or more and 55% or less, said coarse porosity corresponding to a porosity of said coarse voids.
2. The sensor element according to claim 1, wherein said overall porosity is 50% or more and 90% or less.
3. The sensor element according to claim 2, wherein said overall porosity is 60% or more and 90% or less, and said coarse porosity is 10% or more and 55% or less.
4. The sensor element according to claim 3, wherein an area of contact between said inner leading-end protective layer and said element base is 10% or more of a total area of a portion of said element base surrounded by said inner leading-end protective layer.
5. The sensor element according to claim 3, wherein in an overall range of a portion of said element base surrounded by said inner leading-end protective layer, said inner leading-end protective layer has a thickness of 50 μm or more and 1000 μm or less at a position where said inner leading-end protective layer is in contact with said element base.
6. The sensor element according to claim 3, wherein when said inner leading-end protective layer is imaginarily bisected, along a thickness thereof, into a surface side region closer to a surface and a base side region closer to said element base, a coarse porosity ratio x2/x1 is greater than one,
    where x1 is a surface side coarse porosity as a coarse porosity only in the surface side region, x2 is a base side coarse porosity as a coarse porosity only in the base side region.
7. The sensor element according to claim 6, wherein an inequality x2/x1≥2.4 is satisfied.
8. The sensor element according to claim 2, wherein an area of contact between said inner leading-end protective layer and said element base is 10% or more of a total area of a portion of said element base surrounded by said inner leading-end protective layer.
9. The sensor element according to claim 2, wherein in an overall range of a portion of said element base surrounded by said inner leading-end protective layer, said inner leading-end protective layer has a thickness of 50 μm or more and 1000 μm or less at a position where said inner leading-end protective layer is in contact with said element base.
10. The sensor element according to claim 2, wherein when said inner leading-end protective layer is imaginarily bisected, along a thickness thereof, into a surface side region closer to a surface and a base side region closer to said element base, a coarse porosity ratio x2/x1 is greater than one,
    where x1 is a surface side coarse porosity as a coarse porosity only in the surface side region, x2 is a base side coarse porosity as a coarse porosity only in the base side region.
11. The sensor element according to claim 10, wherein an inequality x2/x1≥2.4 is satisfied.
12. The sensor element according to claim 1, wherein an area of contact between said inner leading-end protective layer and said element base is 10% or more of a total area of a portion of said element base surrounded by said inner leading-end protective layer.

13. The sensor element according to claim 12, wherein
in an overall range of a portion of said element base surrounded by said inner leading-end protective layer, said inner leading-end protective layer has a thickness of 50 μm or more and 1000 μm or less at a position where said inner leading-end protective layer is in contact with said element base.

14. The sensor element according to claim 12, wherein
when said inner leading-end protective layer is imaginarily bisected, along a thickness thereof, into a surface side region closer to a surface and a base side region closer to said element base, a coarse porosity ratio x2/x1 is greater than one,
where x1 is a surface side coarse porosity as a coarse porosity only in the surface side region, x2 is a base side coarse porosity as a coarse porosity only in the base side region.

15. The sensor element according to claim 1, wherein
in an overall range of a portion of said element base surrounded by said inner leading-end protective layer, said inner leading-end protective layer has a thickness of 50 μm or more and 1000 μm or less at a position where said inner leading-end protective layer is in contact with said element base.

16. The sensor element according to claim 15, wherein
when said inner leading-end protective layer is imaginarily bisected, along a thickness thereof, into a surface side region closer to a surface and a base side region closer to said element base, a coarse porosity ratio x2/x1 is greater than one,
where x1 is a surface side coarse porosity as a coarse porosity only in the surface side region, x2 is a base side coarse porosity as a coarse porosity only in the base side region.

17. The sensor element according to claim 1, wherein
when said inner leading-end protective layer is imaginarily bisected, along a thickness thereof, into a surface side region closer to a surface and a base side region closer to said element base, a coarse porosity ratio x2/x1 is greater than one,
where x1 is a surface side coarse porosity as a coarse porosity only in the surface side region, x2 is a base side coarse porosity as a coarse porosity only in the base side region.

18. The sensor element according to claim 17, wherein
an inequality $x2/x1 \geq 2.4$ is satisfied.

19. A method for forming a protective layer of a sensor element of a gas sensor, the method comprising:
a preparation step of preparing an element base being a ceramic structured body having a gas inlet in one end portion thereof and including therein a gas distribution part communicating from said gas inlet in a longitudinal direction, a measurement gas containing a gas component to be measured being introduced into said gas distribution part through said gas inlet, said gas component to be measured being sensed by a sensing part disposed in said gas distribution part;
a first formation step of forming an inner leading-end protective layer around an outer periphery of said element base in a predetermined range from said one end portion; and
a second formation step of forming an outer leading-end protective layer having a lower porosity than said inner leading-end protective layer so that said inner leading-end protective layer is covered with said outer leading-end protective layer, wherein
in said first formation step, said element base is dipped in a slurry containing porous pieces each having fine pores with a pore diameter of 10 nm or more and less than 1 μm to attach said slurry to a portion of said element base in a range of formation of said inner leading-end protective layer to thereby form said inner leading-end protective layer:
said inner leading-end protective layer having:
coarse voids with a size of 1 μm or more in a matrix region having a framework structure formed by said porous pieces;
an overall porosity of 40% or more and 90% or less; and
a coarse porosity of 1% or more and 55% or less, said coarse porosity corresponding to a porosity of said coarse voids.

* * * * *